United States Patent [19]

Theobald et al.

[11] Patent Number: 4,562,259

[45] Date of Patent: Dec. 31, 1985

[54] OXADIAZOLYLMETHYLTHIOL PHOSPHATES AS PESTICIDES

[75] Inventors: Hans Theobald; Heinrich Adolphi, both of Limburgerhof; Karl Kiehs, Lampertheim, all of Fed. Rep. of Germany

[73] Assignee: BASF Aktiengesellschaft, Fed. Rep. of Germany

[21] Appl. No.: 280,360

[22] Filed: Jul. 6, 1981

Related U.S. Application Data

[63] Continuation of Ser. No. 125,282, Feb. 27, 1980, abandoned.

[30] Foreign Application Priority Data

Mar. 8, 1979 [DE] Fed. Rep. of Germany ....... 2909013

[51] Int. Cl.⁴ .................... A01N 57/16; A01N 57/24; A01N 57/32; C07F 9/65
[52] U.S. Cl. .................................................. 548/112
[58] Field of Search ................... 548/112; 424/200; 514/92

[56] References Cited

U.S. PATENT DOCUMENTS 3,711,494 1/1973 Adolphi et al. ...................... 548/112
4,028,377 6/1977 Meyer et al. ........................ 424/200
4,073,894 2/1978 Stach et al. ......................... 548/112

FOREIGN PATENT DOCUMENTS 2909013 9/1980 Fed. Rep. of Germany ....... 548/112

OTHER PUBLICATIONS

Rufenacht, "Helvetica Chimica Acta", vol. 55, No. 6, (1972), pp. 1979–1985.

*Primary Examiner*—Anton H. Sutto
*Attorney, Agent, or Firm*—Keil & Weinkauf

[57] ABSTRACT

New 1,3,4-oxadiazolylmethylthiol phosphates and their use for combating pests. The 1,3,4-oxadiazolylmethylthiol phosphates have the formula

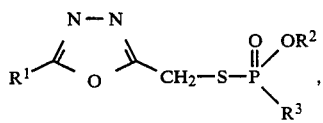

where $R^1$ and $R^2$ are identical or different and each denotes alkyl of up to 6 carbon atoms and $R^3$ denotes alkylthio of up to 6 carbon atoms, amino, or alkylamino or dialkylamino where alkyl is of up to 5 carbon atoms.

6 Claims, No Drawings

OXADIAZOLYLMETHYLTHIOL PHOSPHATES AS PESTICIDES

This is a continuation of application Ser. No. 125,282, filed Feb. 27, 1980, now abandoned.

The present invention relates to new 1,3,4-oxadiazolymethylthiol phosphates, a process for their manufacture, pesticides containing these 1,3,4-oxadiazolylmethylthiol phosphates as active ingredients, and a process for combating pests with these active ingredients.

O,O-Dialkyl-1,34-oxadiazolylmethylthiol phosphates having an insecticidal and acaricidal action have been disclosed (German Laid-Open Application DE-OS No. 1,942,993).

We have found that 1,3,4-oxadiazolylmethylthiol phosphates of the formula

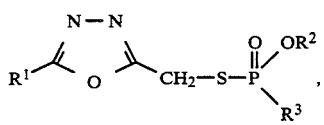

where $R^1$ and $R^2$ are identical or different and each denotes alkyl of up to 6 carbon atoms and $R^3$ denotes alkylthio of up to 6 carbon atoms, amino, or alkylamino or dialkylamino where alkyl is of up to 5 carbon atoms, are more effective on pests from the class of insects, mites and nematodes than the prior art O,O-dialkyl-1,3,4-oxadiazolylmethylthiol phosphates.

$R^1$ and $R^2$ in formula I may be identical or different, and denote linear or branched alkyl of up to 6 carbon atoms, e.g., methyl, ethyl, propyl, butyl, pentyl or hexyl. $R^3$ in formula I denotes linear or branched alkylthio of up to 6 carbon atoms, e.g., methylthio, ethylthio, n-propylthio, isopropylthio, sec-butylthio, isobutylthio, tert-butylthio, 3-methyl-n-butylthio, 2-methyl-n-butylthio, 4-methyl-n-pentylthio, 4-ethyl-n-butylthio, or neopentylthio, or alkylamino or dialkylamino where alkyl is of up to 5 carbon atoms, e.g., methylamino, ethylamino, dimethylamino, diethylamino, n-propylamino, isopropylamino, di-n-butylamino, n-butylamino, n-pentylamino, 3-methyl-n-butylamino, and di-n-pentylamino.

Preferred substituents $R^1$ and $R^2$ are alkyl of up to 3 carbon atoms, such as methyl, ethyl, n-propyl, or isopropyl, especially ethyl, and for $R^3$ alkylthio of up to 4 carbon atoms, such as methylthio, ethylthio, n-propylthio, isopropylthio, n-butylthio, isobutylthio, or sec-butylthio, and alkylamino and dialkylamino where alkyl is of up to 3 carbon atoms, such as methylamino, ethylamino, diethylamino, n-propylamino and isopropylamino.

The 1,3,4-oxadiazolylmethylthiol phosphates of the formula I may be obtained by reaction of 1,3,4-oxadiazolylmethyl halides of the formula II with salts of thiophosphoric acid esters of the formula III in accordance with the following equation:

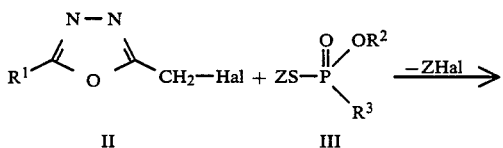

II III

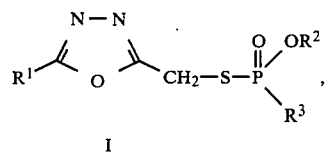

I the radicals $R^1$, $R^2$ and $R^3$ having the above meanings, Hal denoting halogen and Z denoting an alkali metal ion, one equivalent of an alkaline earth metal ion or an ammonium ion which is unsubstituted or substituted by alkyl.

Fluorine, chlorine, bromine and iodine are suitable as halogen, but chlorine and bromine are preferred. Preferred alkali metal ions are sodium and potassium, preferred alkaline earth metal ions are magnesium and calcium, and preferred ammonium ions are the unsubstituted ion and methyl-, ethyl-, propyl-, isopropyl-, dimethyl-, diethyl-, trimethyl-, triethyl-, tetramethyl- and tetraethylammonium.

The reaction is advantageously carried out in solvents or diluents inert to the reactants. Suitable examples are water; alcohols, such as methanol, ethanol and propanol; ethers, such as tetrahydrofuran, dioxane and diglycol dimethyl ether; ketones, such as acetone, methyl ethyl ketone and diethyl ketone; aromatic hydrocarbons, such as toluene, xylenes and chlorobenzenes; nitriles, such as acetonitrile; dimethylformamide; and dimethyl sulfoxide. Mixtures of these solvents or diluents may also be used. When nonaqueous solvents are used, it may be advantageous to add a catalytic amount of potassium iodide to increase the reactivity.

The starting materials are generally employed in equimolar amounts. An excess of the one or the other reaction component may in some cases prove advantageous.

The reaction temperature may be varied within a wide range; generally, the temperature employed is from 0° to 150° C., preferably from 20° to 100° C.

The 1,3,4-oxadiazolylmethyl halides used as starting materials are disclosed in German Laid-Open Applications DE-OS No. 1,942,933 and DE-OS No. 1,962,372 and may be prepared by the processes described therein. A further synthesis route is to react acid hydrazides of the formula IV (known from the literature) with o-chloroacetic acid triethyl esters of the formula V in accordance with the following equation:

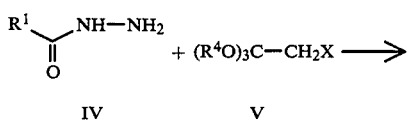

IV V

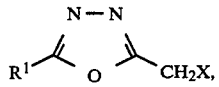

$R^1$ having the above meanings, $R^4$ denoting methyl or ethyl and X denoting bromine or chlorine.

The phosphoric acid salts of the formula III may be prepared by the processes described in Houben-Weyl, Methoden der organischen Chemie, XII/2, 131 et seq., Georg Thieme-Verlag, Stuttgart, 1964, or by the process disclosed in German Laid-Open Application DE-OS No. 2,506,618.

The following examples illustrate the preparation of the 1,3,4-oxadiazolylmethylthiol phosphates. Parts by weight bear the same relationship to parts by volume as kilograms to liters.

EXAMPLE 1

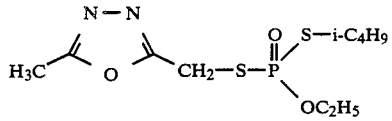

At 110° to 120° C., 222 parts by weight of acetic acid hydrazide is added in portions to 1,118 parts by weight of orthochloroacetic acid triethyl ester and 1 part by weight of orthophosphoric acid; the alcohol which forms is distilled off via a descending condenser. The residue is stirred for 90 minutes at 110° to 120° C. and then fractionated in a column. The fraction distilling over at 73° to 75° C./0.53 mbar is 98% pure 5-methyl-1,3,4-oxadiazolylmethyl chloride. $n_D^{25}$: 1.4758; yield: 77% of theory.

13.3 parts by weight of 5-methyl-1,3,4-oxadiazolylmethyl chloride and 26 parts by weight of dimethylammonium O-ethyl-S-isobutyldithiophosphate are stirred for 6 hours at 80° C. in 100 parts by volume of water and 5 parts by volume of dimethylformamide. After cooling, the oil which has precipitated out is separated and taken up in toluene. The toluene solution is washed with dilute sodium bicarbonate solution and water, and dried over sodium sulfate. The solution is filtered and freed from toluene. The residue is subjected to incipient distillation at 60° C./0.27 mbar. There is obtained 24 parts (77.5%) of theory) of a pale yellow, oily liquid.

$C_{10}H_{19}N_2PO_3S_2$ (310) calc.: C, 38.7; H, 6.2; N, 9.0; P, 10.0; S, 20.7; found: C, 38.8; H, 5.9; N, 8.8; P, 9.9; S, 20.6.

60 MHz nmr spectrum in CDCl$_3$ ($\delta$ values): 1.05 (6H); 1.38 (3H); 1.6–2.3 (1H); 2.55 (3H); 2.81 (2H); 4.0–4.5 (2H+2H).

EXAMPLE 2

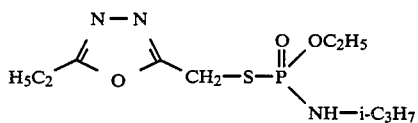

11.7 parts by weight of 5-ethyl-1,3,4-oxadiazolylmethyl chloride and 20 parts by weight of diethylammonium O-ethyl-N-isopropylamidothiophosphate are refluxed for 12 hours with 0.5 part by weight of potassium iodide in 150 parts by volume of acetone. After cooling, the mixture is filtered and concentrated. The residue is taken up in methylene chloride, followed by extraction by shaking with water. After drying over sodium sulfate, the solvent is removed and the residue subjected to incipient distillation at 60° C./0.27 mbar. 22.1 parts (94% of theory) of a pale yellow, oily liquid is isolated.

$C_{10}H_{20}N_3PO_3S$ (293) calc.: C, 41.0; H, 6.9; N, 14.3; S, 10.9; P, 10.6; found: C, 40.8; H, 6.8; N, 14.3; S, 10.8, P, 10.2.

60 MHz nmr spectrum in CDCl$_3$ ($\delta$ values): 1.1–1.55 (3H+6H+3H); 2.88 (2H); 3.2–3.7 (1H); 3.9–4.3 (2H+2H).

The following compounds, for instance, are obtained analogously:

| No. | R$^1$ | R$^2$ | R$^3$ | NMR-data (MHz; solvent) δ-value |
|---|---|---|---|---|
| 3 | CH$_3$ | C$_2$H$_5$ | sec-C$_4$H$_9$—S— | (60; CDCl$_3$) 0.89(3H); 1.05–1.76(3H); 3H + 2H; 2.38(3H); 2.9–3.6(1H); 3.8–4.4(2H + 2H) |
| 4 | CH$_3$ | C$_2$H$_5$ | n-C$_3$H$_7$—S— | (60; CDCl$_3$) 1.02(3H); 1.36(3H); 1.80(2H); 2.54 (3H); 2.5–3.1(2H); 4.1–4.4(2H + 2H) |
| 5 | CH$_3$ | C$_2$H$_5$ | NH—i-C$_3$H$_7$ | (220; CDCl$_3$) 1.0–1.3 (CH + 3H) 2.5(3H); 3.5(1H); 3.9(1H); 4.1–4.3(2H + 2H) |
| 6 | CH$_3$ | C$_2$H$_5$ | N(CH$_3$)$_2$ | (80; CDCl$_3$) 1.3(3H); 2.5 (6H); 2.7(3H); 3.8–4.2 (2H + 2H) |
| 7 | C$_2$H$_5$ | C$_2$H$_5$ | n-C$_3$H$_7$—S— | (60; CDCl$_3$) 1.0(3H); 1.2–1.55(3H + 3H); 1.7(2H); 2.5–3.2(2H + 2H); 3.9–4.5(2H + 2H) |
| 8 | C$_2$H$_5$ | C$_2$H$_5$ | i-C$_3$H$_7$—S— | (60; CDCl$_3$) 1.1–1.6 (3H + 3H + 6H); 2.8(2H); 3.1–3.8(1H); 4.0–4.4(2H + 2H) |
| 9 | C$_2$H$_5$ | C$_2$H$_5$ | H$_3$C—S— | (60; CDCl$_3$) 1.33(3H + 3H); 2.34(3H); 3.8(2H); 4.05–4.4(2H + 2H) |
| 10 | C$_2$H$_5$ | C$_2$H$_5$ | sec-C$_4$H$_9$—S— | (60; CDCl$_3$) 1.05(6H); 1.2–1.6(3H + 3H); 1.7(2H); 2.87 (2H); 3.1–3.6(1H); 4.1–4.4(2H + 2H) |
| 11 | C$_2$H$_5$ | C$_2$H$_5$ | i-C$_4$H$_9$—S— | (60; CDCl$_3$) 1.03(6H); 1.4(6H); 1.7–2.1(1H); 2.6–3.1(2H + 2H) 4.1–4.4(2H + 2H) |
| 12 | C$_2$H$_5$ | C$_2$H$_5$ | N(CH$_3$)$_2$ | (220; CDCl$_3$) 1.25–1.48 (3H + 3H); 2.7(6H); 2.9(2H); 4.1–4.3 (2H + 2H) |
| 13 | i-C$_3$H$_7$— | C$_2$H$_5$ | sec-C$_4$H$_9$—S— | (60; CDCl$_3$) 1.03(3H); 1.8(6H); 1.65(2H); 2.9–3.6(1H + 1H) 4.05–4.4(2H + 2H) |
| 14 | i-C$_3$H$_7$— | C$_2$H$_5$ | i-C$_4$H$_9$—S | (80; CDCl$_3$) 1.0(6H); 1.2–1.5(3H + 6H); 1.9(1H); 2.65–2.95(2H) 2.95–3.3(1H); 4.08–4.35(2H + 2H) |
| 15 | i-C$_3$H$_7$ | C$_2$H$_5$ | n-C$_3$H$_7$—S— | (60; CDCl$_3$) 1.0(3H); 1.2–1.9 (3H + 6H + 2H); 2.6–3.3(2H + 1H); 4.05–4.4(2H + 2H) |
| 16 | i-C$_3$H$_7$ | C$_2$H$_5$ | —NH—i-C$_3$H$_7$ | (220; CDCl$_3$) 1.1(6H); 1.2(3H) 1.3(6H); 3.05(1H); 3.4(1H); 3.85(1H); 3.95–4.1(2H + 2H) |
| 17 | i-C$_3$H$_7$ | C$_2$H$_5$ | N(CH$_3$)$_2$ | (220; CDCl$_3$) 1.3(3H); 1.35(6H); 2.7(6H); 3.2(1H); 4.1–4.25(2H + 2H) |

The 1,3,4-oxadiazolylmethylthiol phosphates according to the invention may be used as pesticides for plant protection and in the hygiene, stores protection and veterinary sectors. They are suitable for effectively combating pests from the class of insects, mites and Nemathelminthes.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae,* and *Pegomya hyoscyami;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Sysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* an example from the Isoptera order is *Reticulitermes lucifugus.*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations or ready-to-use preparations made therefrom, e.g., in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are as follows:

I. 3 parts by weight of O-ethyl-S-isobutyl-S-(5-methyl-1,3,6-oxadiazolyl-2-methyl)-dithiophosphate is intimately mixed with 97 parts by weight of particulate kaolin. A dust is obtained containing 3% by weight of the active ingredient.

II. 30 parts by weight of O-ethyl-S-n-propyl-S-(5-methyl-1,3,4-oxadiazolyl-2-methyl)-dithiophosphate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of O-ethyl-S-n-propyl-S-(5-ethyl-1,3,4-oxadiazolyl-2-methyl)-dithiophosphate is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of O-ethyl-S-n-propyl-S-(5-methyl-1,3,4-oxadiazolyl-2-methyl)-dithiophosphate is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; generally it is from 0.0001 to 10%, preferably from 0.01 to 1%.

The active ingredients may also be successfully used in the ultra-low volume method, where it is possible to apply formulations containing more than 95 wt% of active ingredient, or even the 100% active ingredient (without any additives).

There may be added to the individual active ingredients or mixtures thereof (if desired, immediately before use (tankmix)) oils of various types, herbicides, fungicides, insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, γ-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropane ecarboxylate, -cyano-3-phenoxybenzyl(±)-cis,-trans-2,2-dimethyl-3-(2,2-dichlorovinyl)-cyclopropane carboxylate, (s)- -cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,-trans-chrysanthemate, 2-methyl-5-(2-propynyl)-3-furylmethyl-chrysanthemate, and α-cyano-3-phenoxybenzyl-α-isopropyl-4-chlorophenylacetate.

The following examples illustrate the biological action of the new compounds. The following active ingredients are disclosed in German Laid-Open Application DE-OS No. 1,942,993 and were used for comparison purposes:

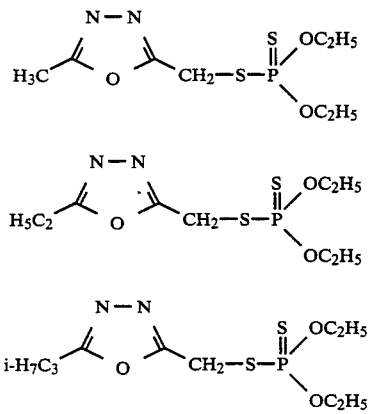

The remaining active ingredients are as listed in the foregoing table.

EXAMPLE A

Contact action on oriental cockroaches (*Blatta orientalis*)

The bottom of 1-liter preserving jars is treated with acetonic solutions of the active ingredients. After the solvent has evaporated, 5 adult cockroaches are placed in each jar.

The kill rate is determined after 48 hours.

| Active ingredient no. | Amount of active ingredients in mg per preserving jar | Kill rate (%) |
|---|---|---|
| 1 | 0.2 | 100 |
|   | 0.1 | 80 |
| 3 | 0.2 | 100 |
|   | 0.1 | 80 |
| 7 | 0.1 | 100 |
| 10 | 0.1 | 100 |
| 13 | 0.1 | 100 |
| 15 | 0.05 | 100 |
| B | 0.25 | 100 |
|   | 0.2 | <80 |
| C | 0.25 | 100 |
|   | 0.2 | <80 |

EXAMPLE B

Continuous contact action on houseflies (*Musca domestica*)

Both the cover and bottom of a Petri dish 10 cm in diameter are lined with a total of 2 ml of acetonic solutions of the active ingredients. After the solvent has evaporated (about 30 minutes), 10 flies are introduced into each dish. The kill rate is determined after 4 hours.

| Active ingredient no. | Amount of active ingredient in mg per dish | Kill rate (%) |
|---|---|---|
| 1 | 0.2 | 100 |
| 3 | 0.2 | 100 |
| 5 | 0.2 | 80 |
| 7 | 0.2 | 100 |
| 8 | 0.2 | 80 |
| 10 | 0.2 | 100 |
| 11 | 0.2 | 80 |
| 13 | 0.2 | 80 |
| B | 0.2 | <50 |

EXAMPLE C

Breeding experiment with houseflies (*Musca domestica*)

50 g of a nutrient medium consisting of 100 parts of water, 10 parts of baker's yeast, 10 parts of dried milk and 1 part of agar is mixed thoroughly, while warm, with aqueous formulations of the active ingredients.

After the medium has cooled, about 0.1 ml of flies' eggs is placed on it, and the development thereof is observed for a week.

The experiment temperature is 20° C.

| Active ingredient no. | Concentration of active ingredient in medium in ppm | Kill rate (%) |
|---|---|---|
| 1 | 0.5 | 100 |
| 3 | 0.4 | approx. 90 |
| 4 | 1.0 | approx. 90 |
| 7 | 0.5 | 100 |
| 10 | 0.5 | approx. 90 |
| 11 | 0.5 | 100 |

-continued

| Active ingredient no. | Concentration of active ingredient in medium in ppm | Kill rate (%) |
| --- | --- | --- |
| 13 | 0.5 | 100 |
| 14 | 0.5 | approx. 90 |
| 15 | 0.2 | approx. 90 |
| A | 2.5 | <50 |
| B | 2.5 | <50 |
| C | 1.0 | <50 |

EXAMPLE D

Contact action and effect of ingested food on caterpillars of the diamondback moth (*Plutella maculipennis*)

Leaves of young cabbage plants are dipped for 3 seconds in aqueous emulsions of the active ingredients and placed, after excess liquid has been briefly allowed to drip off, on a moist filter paper in a Petri dish. 10 caterpillars of the 4th stage of the diamondback moth are then placed on each leaf.

The action is assessed after 48 hours.

| Active ingredient no. | Active ingredient concentration in emulsion (%) | Kill rate (%) |
| --- | --- | --- |
| 1 | 0.02 | 100 |
|   | 0.01 | approx. 80 |
| 3 | 0.02 | 100 |
|   | 0.01 | approx. 80 |
| 4 | 0.02 | 100 |
|   | 0.01 | approx. 80 |
| 7 | 0.02 | 100 |
|   | 0.01 | approx. 80 |
| 10 | 0.002 | 100 |
|   | 0.001 | approx. 80 |
| 13 | 0.005 | 100 |
|   | 0.004 | approx. 80 |
| 14 | 0.004 | 100 |
| A | 0.05 | 100 |
|   | 0.02 | <50 |
| B | 0.025 | 100 |
|   | 0.01 | 50 |
| C | 0.1 | 50 |

EXAMPLE E

Systemic action on caterpillars (*Prodenia litura*)

200 ml of quartz sand is introduced into 250 ml polystyrene beakers which are located in pallets of 8 vessels each. 5 Indian corn seeds are placed in each beaker about 1 cm beneath the surface of the soil. The soil in each beaker is then moistened with 50 ml of water and a transparent plastic cover is then placed over each pallet. The covers are removed after 8 days, and treatment is carried out after 10 days by watering the plants with 40 ml of aqueous active ingredient formulations; after a further day, 50 ml of quartz sand is added to each beaker to prevent the animals from coming into contact with the treated surface.

A plastic cylinder 7 cm in diameter is then placed on each beaker, 5 caterpillars in the 3rd larval stage are introduced into it, and a wire gauze cap is placed on the cylinder.

The kill rate is assessed after 4 days.

| Active ingredient no. | Concentration of active ingredient in formulation (%) | Kill rate (%) |
| --- | --- | --- |
| 1 | 0.05 | 100 |
| 3 | 0.1 | 100 |

-continued

| Active ingredient no. | Concentration of active ingredient in formulation (%) | Kill rate (%) |
| --- | --- | --- |
| 4 | 0.1 | 100 |
| 7 | 0.1 | 100 |
| 10 | 0.1 | 100 |
| 11 | 0.1 | 100 |
| 15 | 0.05 | 100 |
| A | 0.1 | <50 |
| B | 0.1 | <50 |
| C | 0.1 | <50 |

EXAMPLE F

Contact action on aphids (*Aphis fabae*); spray experiment

Potted bean plants (*Vicia faba*) with large aphid colonies are sprayed to runoff in a spray cabinet with aqueous formulations of the active ingredients.

Assessment takes place after 24 hours.

| Active ingredient no. | Concentration of active ingredient in formulation (%) | Kill rate (%) |
| --- | --- | --- |
| 1 | 0.01 | 100 |
| 2 | 0.01 | 100 |
| 3 | 0.005 | 100 |
|   | 0.002 | approx. 80 |
| 5 | 0.01 | 100 |
|   | 0.005 | approx. 80 |
| 10 | 0.01 | 100 |
| 14 | 0.01 | 100 |
| C | 0.01 | approx. 80 |

EXAMPLE G

Contact action on ticks (*Ornithodorus moubata*)

Ticks in the 3rd larval stage are placed in paper bags which are then dipped for 3 seconds in the emulsions. The bags are then suspended. The action on the ticks is assessed after 48 hours.

| Active ingredient no. | Concentration of active ingredient in emulsion (%) | Kill rate (%) |
| --- | --- | --- |
| 4 | 5 | 100 |
| 10 | 5 | 100 |
| 11 | 4 | 100 |
| 13 | 10 | 100 |
| 14 | 10 | 100 |
| A | 25 | 100 |
|   | 10 | <50 |
| C | 50 | 100 |
|   | 25 | <50 |

EXAMPLE H

Action on root-knot nematodes (*Meloidogyne incognita*)

20 ml of aqueous formulations of the active ingredients is poured onto 500 g of compost heavily infested with root-knot nematodes.

The roots are assessed as to cyst formation after 6 to 8 weeks.

| Active ingredient no. | Concentration of active ingredient in formulation (%) |  |
| --- | --- | --- |
| 2 | 0.01 | no cyst formation |
| 7 | 0.025 | " |
| 8 | 0.02 | " |

-continued

| Active ingredient no. | Concentration of active ingredient in formulation (%) | |
|---|---|---|
| 10 | 0.025 | " |
| 11 | 0.05 | " |
| 13 | 0.02 | " |
| 14 | 0.05 | " |

We claim:

1. A 1,3,4-oxadiazolylmethylthiol phosphate of the formula

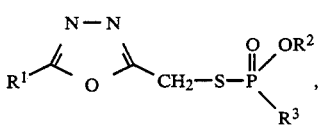

where $R^1$ and $R^2$ are identical or different and each denotes alkyl of up to 6 carbon atoms and $R^3$ denotes alkylthio of up to 6 carbon atoms, amino, or alkylamino or dialkylamino where alkyl is of up to 5 carbon atoms.

2. O-Ethyl-S-n-propyl-S-(5-methyl-1,3,4-oxadiazolyl-2-methyl)-dithiophosphate.

3. O-Ethyl-S-isobutyl-S-(5-methyl-1,3,4-oxadiazolyl-2-methyl)-dithiophosphate.

4. O-Ethyl-S-sec-butyl-S-(5-methyl-1,3,4-oxadiazolyl-2-methyl)-dithiophosphate.

5. A pesticide comprising a solid and/or liquid carrier and from 0.5 to 90% by weight based on the total pesticide weight of a 1,3,4-oxadiazolylmethylthiol phosphate as defined in claim 1.

6. A process for combating pests, wherein an insecticidally, acaricidally or nematocidally effective amount of a 1,3,4-oxadiazolylmethylthiol phosphate of the formula I as defined in claim 1 is allowed to act on the pests or their biotope.

* * * * *